United States Patent [19]
Harvey et al.

[11] Patent Number: 5,756,360
[45] Date of Patent: May 26, 1998

[54] METHOD AND APPARATUS FOR PROVIDING DILUTED GAS TO EXHAUST EMISSION ANALYZER

[75] Inventors: R. Neal Harvey, Santa Ana; Allen F. Dageforde, Orange, both of Calif.

[73] Assignee: Horiba Instruments Inc., Irvine, Calif.

[21] Appl. No.: 536,401

[22] Filed: Sep. 29, 1995

[51] Int. Cl.$^6$ ................................................ G01N 1/14
[52] U.S. Cl. .................... 436/179; 73/1 G; 73/23.31; 73/863.03; 73/863.83; 422/83; 422/94; 436/134; 436/181
[58] Field of Search .............. 422/94, 83; 436/134, 436/177, 179, 181; 73/23.31, 1 G, 31.02, 31.03, 863.02, 863.03, 863.11, 863.83, 864.34, 864.81, 863.61

[56] References Cited

U.S. PATENT DOCUMENTS

| | | |
|---|---|---|
| 3,144,769 | 8/1964 | Franscisco, Jr. |
| 3,407,646 | 10/1968 | Traver. |
| 3,593,023 | 7/1971 | Dodson et al. |
| 3,603,155 | 9/1971 | Morris et al. |
| 3,699,814 | 10/1972 | Kaufman. |
| 3,784,902 | 1/1974 | Huber. |
| 3,817,100 | 6/1974 | Anderson et al. |
| 3,965,749 | 6/1976 | Hadden et al. |
| 3,986,386 | 10/1976 | Beltzer et al. |
| 4,226,675 | 10/1980 | Lewis et al. |
| 4,254,797 | 3/1981 | Mayeaux. |
| 4,351,181 | 9/1982 | Currans. |
| 4,379,402 | 4/1983 | Harman, III. |
| 4,498,496 | 2/1985 | Barcellona et al. |
| 4,555,930 | 12/1985 | Leach et al. |
| 4,555,931 | 12/1985 | Amimoto et al. ............ 73/23.31 |
| 4,586,367 | 5/1986 | Lewis. |
| 4,660,408 | 4/1987 | Lewis. |
| 4,823,591 | 4/1989 | Lewis. |
| 4,852,384 | 8/1989 | Woolbert et al. |
| 4,977,776 | 12/1990 | Shindo et al. |
| 5,129,297 | 7/1992 | Carduner et al. ............ 73/23.31 |
| 5,157,957 | 10/1992 | Mettes et al. |
| 5,184,501 | 2/1993 | Lewis et al. |
| 5,337,595 | 8/1994 | Lewis. |
| 5,410,907 | 5/1995 | Ström et al. ............ 73/23.31 |
| 5,469,731 | 11/1995 | Decker et al. ............ 73/23.31 |
| 5,650,565 | 7/1997 | Nagy et al. |

*Primary Examiner*—Jan Ludlow
*Attorney, Agent, or Firm*—Brooks & Kushman P.C.

[57] ABSTRACT

An apparatus and method are adapted for analyzing exhaust emissions by using a small fraction of a continuously-extracted exhaust sample combined with a pollutant-free diluent through a system of critical flow orifices at a predetermined and precisely controlled flow ratio. A small quantity of gas is extracted from the diluted exhaust gas available which is diluted with the contaminant-free air or nitrogen to produce a mixture having a dew point below ambient air temperature and satisfying the flow requirements of the analysis system.

24 Claims, 2 Drawing Sheets

METHOD AND APPARATUS FOR PROVIDING DILUTED GAS TO EXHAUST EMISSION ANALYZER

BACKGROUND OF THE INVENTION

This invention relates to a gas sampling device to measure the concentration of exhaust substances (i.e., emissions of, for example, CO, $CO_2$, hydrocarbons HC, $NO_x$, $SO_x$ and the like) contained in the exhaust gas of an automotive vehicle.

A conventional method of measuring the mass of components in exhaust gases uses the CVS (Constant Volume Sampling) method. The CVS method continuously dilutes all of the exhaust gases from an engine with ambient air to a constant and known volume flow rate. The constant flow rate is controlled by drawing the diluted exhaust gases through a volumetric measuring device such as a critical flow venturi or a positive displacement pump. By continuously collecting a small fraction of the total diluted flow in a bag during a test cycle, the mass of a component can be determined by measuring the concentration of the component in the bag at the end of a test and multiplying by the total diluted volumetric flow measured during the test. The CVS method works well as long as the concentration of the component measured is large compared to the concentration of that component in the dilution air. As progress is being made in the reduction of mass pollutants emitted from an engine, the contribution made to the measurement by the diluent is no longer negligible. In fact, sometimes the concentration of a pollutant in the diluent air is larger than the concentration in the exhaust gas. An obvious solution to this situation is to use a purified diluent instead of ambient air. For the CVS technique, this is an expensive and impractical approach because of the large volumes of diluent required. Typically the minimum volume of diluent required is eight to ten times the maximum instantaneous exhaust gas flow rate. This large quantity of diluent is necessary in order to reduce the dew point of the gas mixture to below ambient temperature, thereby preventing condensation of the moisture present in the exhaust gas.

An alternate technique to measure mass emissions and avoid measuring the pollutants in the dilution air is to measure the exhaust concentrations before CVS dilution and separately determine the exhaust mass flow. Additional flow measurements must be made to utilize the CVS method.

To determine the instantaneous mass flow of an exhaust component using the CVS method, the following technique can be used. The instantaneous exhaust gas flow rate can be calculated by measuring the diluent flow rate into the CVS with a flow measurement device such as a smooth approach orifice and mathematically subtracting this from the CVS flow rate. By using the instantaneous exhaust flow rate and the undiluted exhaust concentrations the instantaneous mass emissions of any component may be determined.

In order to measure the concentration of exhaust gas components directly, analysis must either be done at elevated temperatures in specially designed instrumentation or the water which condenses when the exhaust gas is cooled must be removed before analysis. Both of these approaches have disadvantages. Instruments designed to operate at elevated temperatures are expensive and usually require considerable care and maintenance. Analysis on a "wet basis" is desirable to eliminate the errors introduced by removing the water from the sample. When the water vapor in the gas is condensed and removed, some of the pollutants are removed with the water. The concentrations indicated when analyzing a sample on a "dry basis" are higher than "wet basis" analysis due to the decrease in volume caused by removal of the water. The "wet basis" analysis can only be approximated from the "dry basis" analysis. The residual errors are undesirable.

According to the present invention, a small quantity of undiluted exhaust gas is extracted and diluted with contaminant-free air or nitrogen producing a mixture having a dew point below ambient temperature and satisfying the flow requirements of the analysis system. Analysis is performed at ambient temperature without water extraction or loss of any exhaust emissions components using a small quantity of diluent gas. The undiluted concentrations are readily obtained by multiplying the diluted sample concentrations by the dilution ratio.

SUMMARY OF THE INVENTION

This invention is adapted to be used for analyzing exhaust emissions by using a small fraction of a continuously-extracted exhaust sample combined with a pollutant-free diluent through a system of critical flow orifices at a predetermined and precisely controlled flow ratio. The apparatus and method of the present invention includes the general steps of: (1) Establishing the working dilution ratio; (2) introducing calibration gases to establish the operating-dilution ratio; (3) extracting an aliquot of high dew point exhaust gas; (4) diluting the exhaust gas sample with a dry, pollutant-free diluent; (5) maintaining the exhaust gas at a temperature above the dew point of water through dilution; and (6) delivering the diluted exhaust gas to the analysis system at a sufficient flow rate to satisfy the flow requirements of the gas analysis system. Once delivered to the analyzer, the diluted gas can then be analyzed and the undiluted pollutant concentrations obtained by multiplying the dilution ratio.

According to the present invention, sample and diluent flow orifices have throat sizes that are properly sized to accurately control the dilution ratio of exhaust gas to diluent gas. The inlet pressure to the diluent orifice is controlled to a pressure equal to the sample orifice inlet pressure by a pneumatic relay. The sample and diluent orifices exit into a common reduced pressure manifold. The manifold pressure is maintained at a reduce pressure sufficient to create critical flow through both orifices. By situating the orifices and related fluid lines within an oven, the temperature of the sample is maintained above the dew point of exhaust gas, thus eliminating condensation problems. This oven arrangement also maintains the orifices at equal temperatures, thus circumventing dilution ratio variations.

The sample and diluent orifices are preferably of the critical flow variety, however (or alternately) critical flow venturis, subsonic orifices, or subsonic venturis may be substituted for the critical flow orifices. The invention maintains constant dilution ratio with subsonic orifices and subsonic venturis by maintaining equal pressure at the inlets and equal, reduced pressure at the outlets of the sample and dilution orifices or venturis.

DETAILED DESCRIPTION OF THE PREFERRED EMBODIMENT

Figure 1:
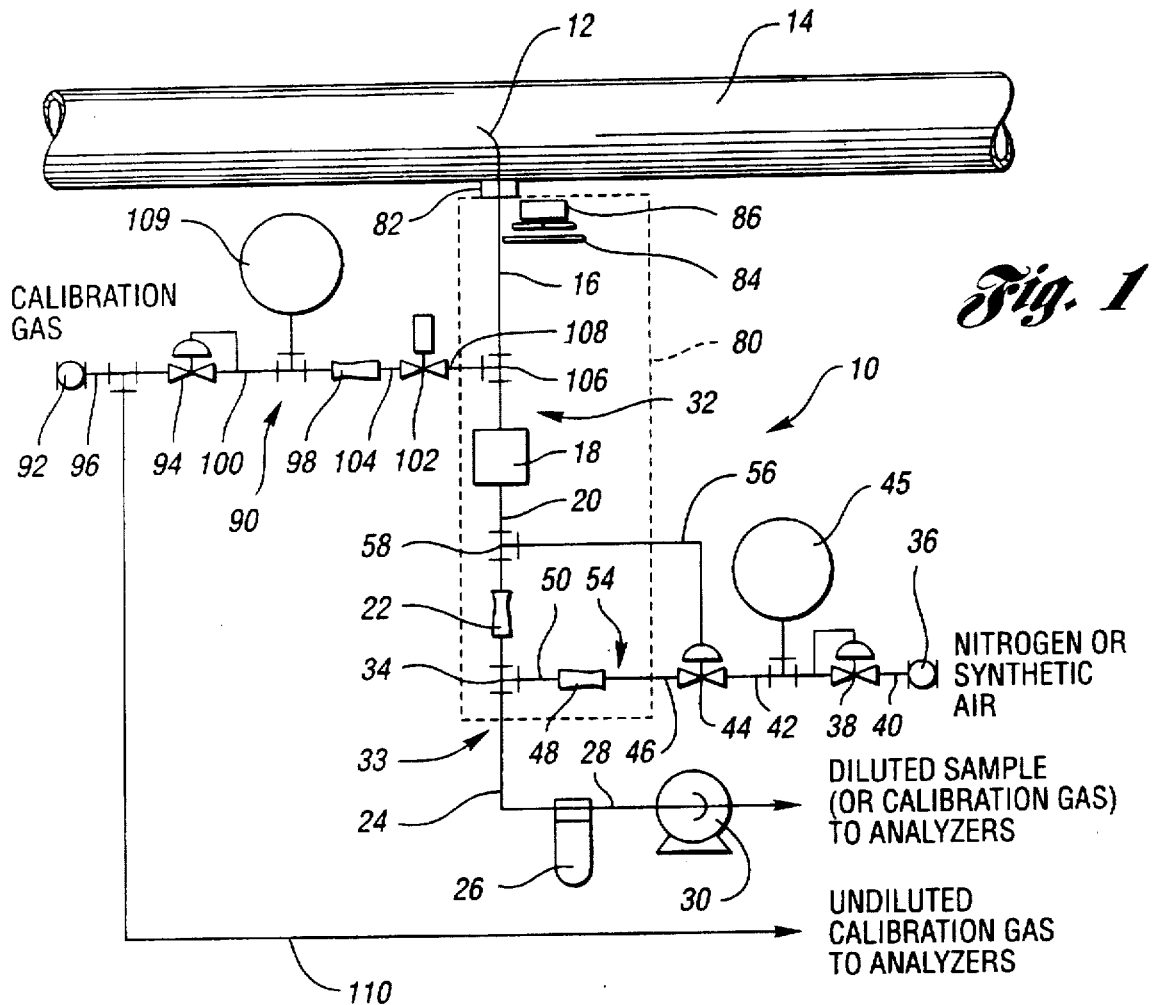
FIG. 1 is a diagrammatic illustration of a system for providing diluted gas to an exhaust emission analyzer constructed in accordance with a preferred embodiment of the present invention.

Referring now to FIG. 1. a pneumatically-operated apparatus for providing diluted exhaust gas to an exhaust emission analyzer is depicted and is identified generally by the reference numeral 10. The apparatus 10 comprises a tail pipe adapter 12 for coupling to an internal combustion engine exhaust pipe 14. Exhaust from the exhaust pipe 14 is introduced through an exhaust sample inlet line 16. The sample inlet line 16 terminates at a prefilter 18. The inlet line 16 as well as all of the other fluid lines of the present invention are preferably composed of stainless steel for corrosion resistance. The prefilter 18 is provided to eliminate particulates from the exhaust sample, the presence of which would otherwise build up on the critical flow surfaces of the apparatus 10. The prefilter 18 is of any type known in the art that is capable of removing particulates.

The exhaust sample exits the prefilter 18 into a prefilter outlet line 20 which forms a connector between the prefilter 18 and, according to the preferred embodiment of the apparatus illustrated in FIG. 1. a sample critical flow orifice or critical flow venturi 22. As is known, the venturi includes a convergent cone and a divergent cone with a throat therebetween. At the outlet side of the sample orifice 22 is a first bulkstream line 24 which fluidly connects the sample orifice 22 with a pulsation dampener 26. The dampener 26 is located in the sample path downstream of the sample orifice 22 but upstream of the sample analyzer (not shown). A second bulkstream line 28 connects the dampener 26 to a vacuum pump 30. The dampener 26 dampens or smooths pulsations produced by the pump 30.

The exhaust sample inlet line 16, the prefilter 18, the prefilter outlet line 20, and the sample orifice 22 define a sample fluid path, generally illustrated as 32. The first bulkstream line 24, the pulsation dampener 26, and the second bulkstream line 28 define a bulkstream path generally illustrated as 33.

A quantity of pollutant-free diluent gas (such as nitrogen or air) is introduced into the sample path 32 at a fluid junction 34, which is a point that is downstream of the sample orifice 22. A source of gas, generally illustrated as 36, provides the diluent necessary for proper operation of the apparatus 10.

A key feature of the present invention is the ability to control the dilution ratio by utilizing a pressure relay or regulator on the diluent. An emission analyzer typically requires between four to ten cubic feet per hour to operate. Because the typical emissions analysis system may comprise seven or eight analyzers, the total flow rate requirements may reach 45 to 50 cubic feet per hour. For gasoline-fueled engines, the optimum dilution ratio is approximately 8:1, this being defined as eight parts diluent to one part exhaust gas.

The diluent gas is delivered to a pressure regulator 38 via a first diluent connecting line 40. The diluent pressure regulator 38 reduces the nitrogen or air from the source of gas 36 to a working level of pressure. A second diluent connecting line 42 connects the diluent pressure regulator 38 to a diluent pneumatic relay 44. A pressure gauge 45 is provided on the line 42 to indicate diluent supply pressure. A third diluent connecting line 46 is fitted between the diluent pneumatic relay 44 to a diluent critical flow orifice or critical flow venturi 48. A fourth diluent connecting line 50 fluidly connects the diluent orifice 48 to the first bulkstream line 24 at the fluid junction 34. The first, second, third and fourth diluent connecting lines 40, 42, 46 and 50, respectively, combined with the pressure regulator 38 and the diluent pneumatic relay 44, respectively, the pressure gauge 45 and the diluent orifice or venturi 48 define a diluent path, generally illustrated as 54. A pressure reference line 56 connects the diluent pneumatic relay 44 with the prefilter outlet line 20 at a fluid junction 58 at a point that is upstream of the sample orifice 22. The diluent pneumatic relay 44 senses the pressure at the inlet of the sample orifice 22 through line 56 and controls the pressure at the inlet side of the diluent orifice 48 such that it is equal to the sample pressure entering the sample orifice 22.

Figure 2:
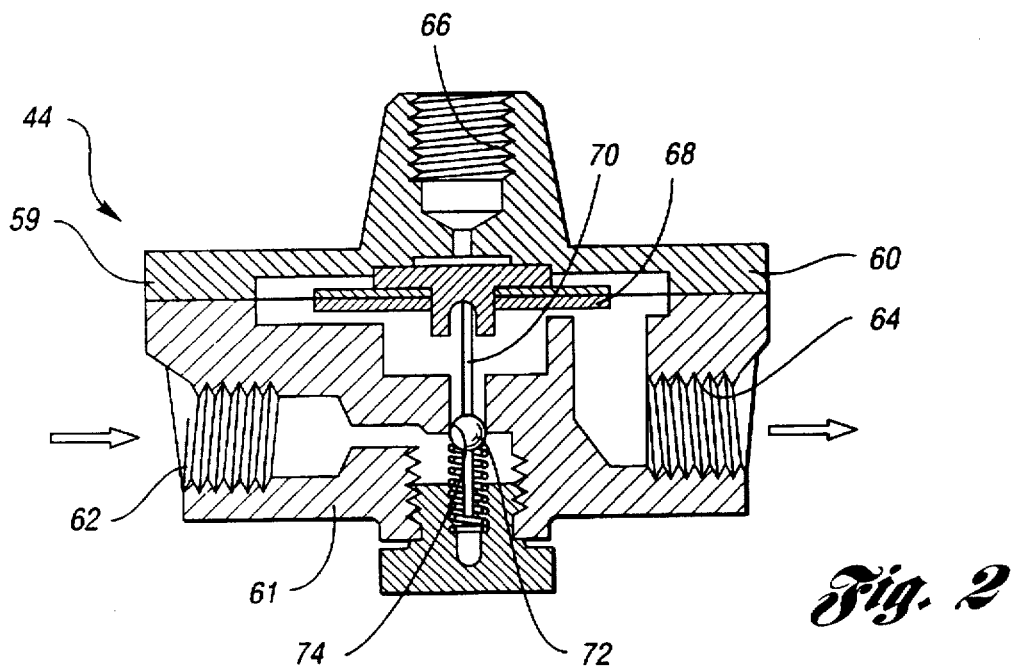
FIG. 2 is a sectional view of a preferred pneumatic relay of the present invention.

The diluent pneumatic relay 44, illustrated in sectional view in FIG. 2, is a modified version of a known pressure regulator, such as Model 63SD Flow Controller sold by Moore Products. This relay is critical in that it controls the diluent pressure at the inlet to the dilution orifice 48 so that it is at the same pressure as the exhaust sample. The relay 44 includes a body 59 having an upper body half 60 and a lower body half 61. The lower body half 61 has a diluent gas inlet 62 and a diluent gas outlet 64 formed therein. A diaphragm 68 includes a downward-depending stem 70 having a valve member 72. The member 72 is selectively movable off of a seat 74, and, when so moved, allows gas to pass between the inlet 62 and the outlet 64. The pressure of the gas entering the reference inlet 66 controls movement of the diaphragm 68 and, consequently, flow of the diluent gas through the relay 44. (The above-mentioned Model 63SD has been modified by the removal of a spring [not shown] from between the diaphragm 68 and the inner wall of the upper half of the body 60.)

The pump 30 provides appropriate vacuum to establish the flow of the sample gas through the sample path 32, the diluent path 54, and the bulkstream path 33. The throats of the sample and diluent orifices 22 and 48, respectively, are sized in order to properly control the flows of the exhaust gas and the diluent gas. Preferably, the throat diameter of these orifices range from 0.1 mm to 1.5 mm. Generally, the inlet and outlet pressures to and from the orifices 22 and 48 are controlled to force gas to flow at a sonic velocity (the critical flow). The flow-through of the orifices 22 and 48 is determined according to the following formula:

$$\text{Critical flow-through} = \frac{C \times P}{\sqrt{T}}$$

Where:

C is a constant of proportionality;

P is the absolute pressure at the inlet of the orifice; and

T is the absolute temperature at the inlet.

So long as the absolute pressures at the inlet and outlet of the critical flow orifices 22 and 48 satisfy the relationship defined by $$\frac{P_2}{P_1} < \left(\frac{2}{K+1}\right)^{\frac{k}{k-1}}$$

critical flow (sonic velocity) is present through the orifices. $P_2$ is the absolute pressure at the outlet from a given orifice; $P_1$ is the absolute pressure at the inlet to a given orifice; and K is the ratio of the specific heat at constant pressure to the specific heat at constant volume for the gases flowing through the orifices (K is termed "adiabatic exponent"). See John K. Vennard, *Elementary Fluid Mechanics*, John Wiley and Sons, Inc., 1961, pages 9, 10, 157.

According to the preferred embodiment, the inlet pressure to the diluent orifice 48 is controlled to a pressure equal to the pressure at the inlet of the sample orifice 22. The pressure at the inlet of the orifice 22 may typically range between −1 p.s.i.g. and 4 p.s.i.g. Because the sample and diluent orifices 22 and 48, respectively, exit into the common bulkstream path 33, equal pressure drops are produced across the two orifices 22 and 48, even during transient sample pressure events. Accordingly, at all times the flow rates through the two orifices 22 and 48 are at a constant ratio, preferably in the range of approximately 8 parts diluent to 1 part exhaust sample.

To assist in assuring constant volume ratios and to circumvent dilution ratio variations, the orifices 22 and 48 are maintained at a constant elevated temperature (typically between 160–180 degrees F.), thus eliminating the possibility that the orifices 22 and 48 operate at different temperatures. An oven 80, illustrated by broken lines, is provided for this purpose. The oven 80 includes an extension sleeve 82 and further includes a source of heat 84 (such as a heating coil) and an air bath stirrer 86 (such as a fan) for evenly circulating the warm air within the interior of the oven 80.

In addition to maintaining the orifices 22 and 48 at substantially equal elevated temperatures, the provision of the oven 80 also assures that the temperature of the exhaust gas sample is maintained at a level which is above the dew point of exhaust gas. In engine exhaust, water is present in the exhaust as a combustion product of fuel. The water vapor in the exhaust would ordinarily condense if the exhaust gas were simply cooled to ambient air temperature before analysis, an undesirable condition in that the condensed water interferes with the analysis and, in addition, would undesirably remove some of the pollutants (such as $NO_2$) before analysis. The present system of maintaining the sample at a temperature above the dew point until after dilution (the sample and diluent gases are combined at the junction 34 which is situated within the oven 80) coupled with using a dry diluent gas avoids this problem. Dilution of the sample exhaust gas reduces the dew point to below ambient temperature. Once dilution is completed, the bulkstream gas exits the oven 80 and is allowed to cool to ambient temperature prior to analysis.

To determine the working dilution ratio (the ratio of sample flow rate plus diluent flow rate divided by sample flow rate) established by the orifices 22 and 48, a calibration system, indicated generally as 90, is provided. The system 90 includes a calibration gas source 92, a pressure regulator 94 connected to the gas source 92 by a first line 96, a critical flow orifice 98 connected to the pressure regulator 94 by a second line 100, and a solenoid valve 102 connected with the critical flow orifice 98 by a third line 104. The solenoid valve 102 is connected to the sample inlet line 16 at a junction 106 by a fourth calibration line 108 at a point upstream from the prefilter 18. A pressure indicator 109 is fitted to the second line 100. A direct line 110 is provided between the source 92 and the analyzer (not shown).

By opening the solenoid valve 102 and with an excess flow rate of calibrating gas (in excess of what the apparatus 10 actually draws from the exhaust pipe 14), the calibrating gas flows into the sample orifice 22 and excess calibrating gas "overflows" through the sample inlet line 16 and into the exhaust pipe 14. This floods the inlet side of the sample orifice 22 with calibration gas and assures that a 100% concentration of calibrating gas is passing through the orifice 22. Thereafter, the calibrating gas concentration is diluted by the set ratio created by the two orifices 22 and 48. The diluted calibrating gas can then be analyzed. By allowing a quantity of undiluted calibrating gas to flow directly from the source 92 through the calibration line 110 to the analyzer for analysis, the undiluted concentration is determined. The ratio of these two concentrations establishes the operating-dilution ratio of the system.

Figure 3:
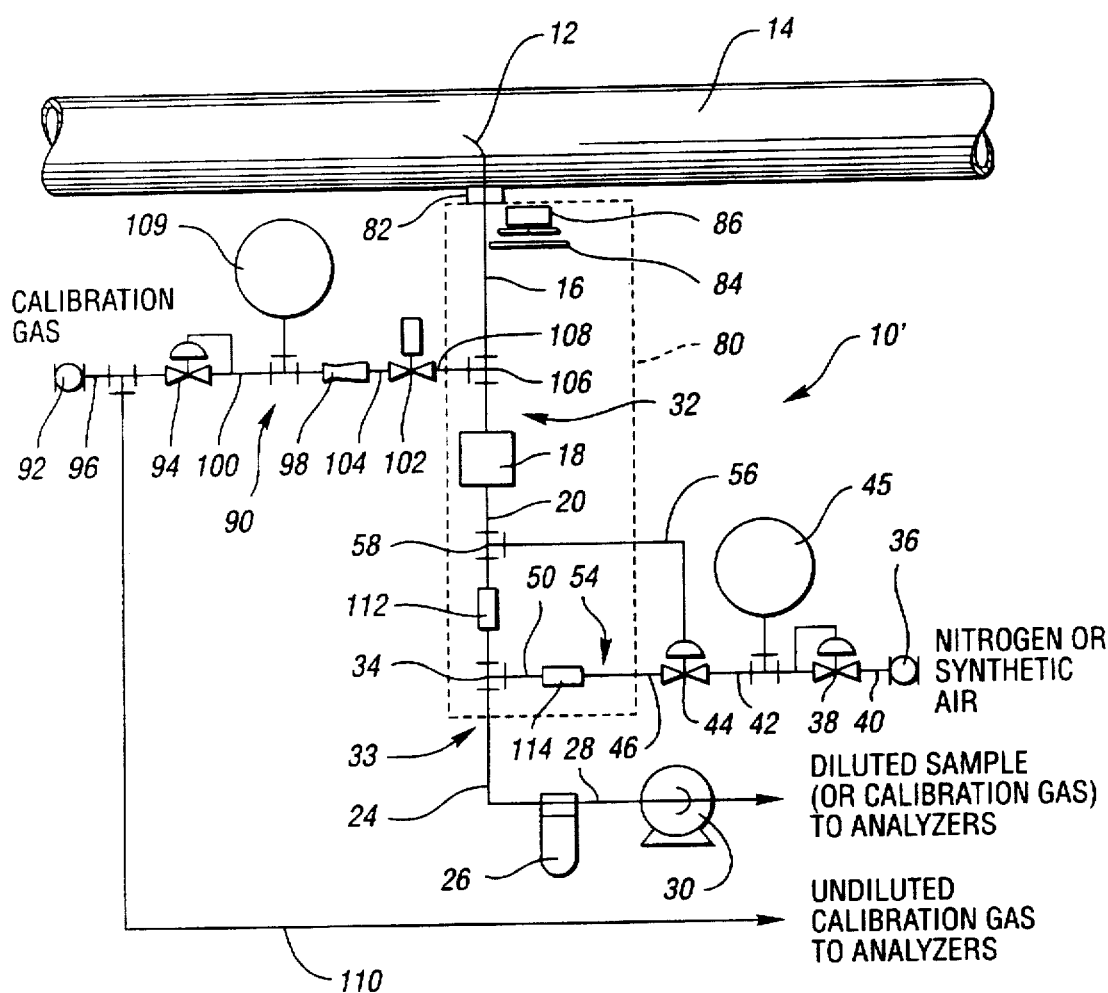
FIG. 3 is a diagrammatic illustration of a system for providing diluent gas similar to the system of FIG. 1 constructed in accordance with an alternate embodiment of the present invention.

An alternate embodiment of the present invention is set forth in FIG. 3, where an apparatus for providing diluent gas to an exhaust emission analyzer is depicted and is identified generally by the reference number 10'. The apparatus 10' is substantially identical to the apparatus 10 shown in FIG. 1 and described in relation thereto, but includes a sample flow control valve 112 in lieu of the sample orifice 22 of FIG. 1 and a diluent flow control valve 114 in lieu of the diluent critical flow orifice 48. The flow control valve may be adjusted manually or electronically. Calibration and operation of the apparatus 10' is substantially identical with that of the apparatus 10.

The arrangement of the present invention provides reliable, controllable, and accurate sample-diluent ratio control. In addition, the system described above is effective within a wide range of exhaust pressures. Tests conducted have demonstrated that the exhaust pressure may be quickly varied from near-atmospheric to about 10 p.s.i.g., and back to atmospheric pressure with the dilution ratio being accurately maintained.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. An apparatus for controlling the dilution of an exhaust gas sample from the exhaust system of an engine for analysis by an exhaust emission analyzer, the apparatus comprising:

an exhaust gas sampling line having first and second ends, said first end being fluidly connected to the exhaust system of the engine;

an exhaust gas sampling line orifice fitted to said exhaust gas sampling line, said exhaust gas sampling line orifice having an inlet;

a source of substantially pollutant-free diluent gas;

a diluent line having first and second ends, said first end being connected to said source of substantially pollutant-free diluent gas;

a diluent line orifice fitted to said diluent line, said diluent line orifice having an inlet, and said exhaust gas sampling line orifice and said diluent line orifice being configured so as to produce equal pressure drops thereacross;

a diluent pressure regulator fitted to said diluent line and connected to said exhaust gas sampling line for controlling pressure such that pressure at said diluent line orifice inlet is equal to pressure at said exhaust gas sampling line orifice inlet;

a diluted gas outlet line having first and second ends, said first end being connected to the exhaust emission analyzer;

a fluid junction, said second ends of said exhaust gas sampling line, said diluent line, and said diluted gas outlet line being connected to said fluid junction; and means for drawing diluted gas through said diluted gas outlet line.

2. The apparatus of claim 1 wherein each of said orifices is a critical flow orifice.

3. The apparatus claim 1, wherein each of said orifices is a critical flow venturi.

4. The apparatus of claim 1, wherein each of said orifices is a subsonic venturi.

5. The apparatus of claim 1, wherein each of said orifices is a subsonic orifice.

6. The apparatus of claim 1, wherein said means for drawing diluted gas comprises a vacuum pump.

7. The apparatus of claim 1, further including a heating oven at least partially enclosing said exhaust gas sampling line, said diluent line, said fluid junction, said exhaust gas sampling line orifice and said diluent line orifice.

8. The apparatus of claim 1, wherein said exhaust gas sampling line further includes a prefilter.

9. The apparatus of claim 1, wherein said diluted gas outlet line further includes a filter.

10. The apparatus of claim 1, further including a calibration line fitted to said exhaust gas sampling line for establishing the operating-dilution ratio of said diluent gas to the exhaust gas sample established by said diluent line orifice and said exhaust gas sampling line orifice.

11. The apparatus of claim 10, further including a source of calibrating gas and wherein said calibration line includes first line connecting said source of calibrating gas to said exhaust gas sampling line and a second line connecting said source of calibrating gas to the exhaust gas analyzer.

12. A method for preparing a sample of exhaust gas from the exhaust system of an engine for analysis by an exhaust emission analyzer, said method including the steps of:

extracting an exhaust gas sample from the exhaust system of an engine and passing said exhaust gas sample through an inlet of an exhaust gas sampling line orifice fitted to an exhaust gas sampling line;

extracting a diluent gas from a diluent gas source and passing said diluent gas through an inlet of a diluent line orifice fitted to a diluent line having a pressure regulator;

maintaining the volumetric ratio of said exhaust gas sample and said diluent gas at a substantially constant rate with said pressure regulator by controlling pressure such that pressure at said diluent line orifice inlet is equal to pressure at said exhaust gas sampling line orifice inlet;

introducing said diluent gas into said exhaust gas sample to create a diluted exhaust gas sample; and directing said diluted exhaust gas sample to the exhaust emission analyzer.

13. The method of claim 12, further including the step of controlling the temperature of said diluent gas and said exhaust gas sample prior to and during the step of introducing said diluent gas into said exhaust gas sample.

14. The method of claim 12, further including the step of controlling the pressure of said diluent gas so that it is substantially at the same pressure as said exhaust gas sample.

15. The method of claim 12, further including the step of establishing a dilution ratio between said diluent gas and said exhaust gas sample.

16. The method of claim 15, further including the step of calibrating the exhaust emission analyzer in response to said dilution ratio.

17. An apparatus for controlling the dilution of an exhaust gas sample from the exhaust system of an engine for analysis by an exhaust emission analyzer, the apparatus comprising:

an exhaust gas sampling line having first and second ends, said first end being fluidly connected to the exhaust system of the engine;

an exhaust gas sampling line flow control valve fitted to said exhaust gas sampling line, said exhaust gas sampling line flow control valve having an inlet;

a source of substantially pollutant-free diluent gas;

a diluent line having first and second ends, said first end being connected to said source of substantially pollutant-free diluent gas;

a diluent line flow control valve fitted to said diluent line, said diluent line flow control valve having an inlet and said exhaust gas sampling line flow control valve and said diluent line flow control valve being configured so as to produce equal pressure drops thereacross;

a diluent pressure regulator fitted to said diluent line and connected to said exhaust gas sampling line for controlling pressure such that pressure at the diluent line flow control valve inlet is equal to pressure at the exhaust gas flow control valve inlet;

a diluted gas outlet line having first and second ends, said first end being connected to the exhaust emission analyzer;

a fluid junction, said second ends of said exhaust gas sampling line, said diluent line, and said diluted gas outlet line being connected to said fluid junction; and means for drawing diluted gas through said exhaust gas sampling line, said diluent line, and said diluted gas outlet line.

18. The apparatus of claim 17, further including a pressure reference line between said pressure regulator and said exhaust gas sampling line.

19. The apparatus of claim 17, further including a heating oven at least partially enclosing said exhaust gas sampling line, said diluent line, said bulkstream line, said diluent connecting line, said diluent line orifice and said exhaust gas sampling line orifice, said heating oven set at a temperature sufficient to prevent condensation.

20. The apparatus of claim 17, wherein each of said orifices is a critical flow orifice.

21. The apparatus of claim 17, wherein each of said orifices is a critical flow venturi.

22. The apparatus of claim 17, wherein each of said orifices is a subsonic flow orifice.

23. The apparatus of claim 17, wherein each of said orifices is a subsonic flow venturi.

24. An apparatus for controlling the dilution of an exhaust gas sample from the exhaust system of an engine for analysis by an exhaust emission analyzer, comprising:

an exhaust gas sampling line having first and second ends, said first end being fluidly connected to the exhaust system of the engine;

an exhaust gas sampling line orifice fitted to said second end of said exhaust gas sampling line, said exhaust gas sampling line orifice having an inlet and an outlet;

a source of substantially pollutant-free gas;

a diluent line having first and second ends, said first end being connected to said source of substantially pollutant-free diluent gas;

a diluent line orifice fitted to said second end of said diluent line, said diluent line orifice having an inlet and an outlet and said diluent line orifice and said exhaust gas sampling line orifice being configured so as to produce equal pressure drops thereacross;

a diluent pressure regulator fitted to said diluent line and connected to said exhaust gas sampling line orifice inlet for controlling pressure such that pressure at said diluent line orifice inlet is equal to pressure at said exhaust gas sampling line inlet;

a bulkstream line having first and second ends, said first end being fluidly connected to said outlet of said exhaust gas sampling line orifice;

a diluent connecting line having first and second ends, said first end being fluidly connected to said outlet of said diluent line orifice;

a fluid junction connected to said second end of said diluent connecting line and said second end of said bulkstream line, such that the exhaust gas sample is diluted at a constant ratio with said substantially pollutant-free diluent gas to produce a diluted exhaust gas sample;

a diluted gas sampling line having first and second ends, said first end being fluidly connected to said fluid junction and said second end being fluidly connected to the exhaust emission analyzer; and means for drawing said diluted exhaust gas sample through said exhaust gas sampling line.

\* \* \* \* \*

UNITED STATES PATENT AND TRADEMARK OFFICE
CERTIFICATE OF CORRECTION

PATENT NO : 5,756,360
DATED : May 26, 1998
INVENTOR(S) : Harvey et al.

It is certified that error appears in the above-identified patent and that said Letters Patent is hereby corrected as shown below:

Column 8, Line 30, Claim 18, Delete "17" and insert "24".

Column 8, Line 33, Claim 19, Delete "17" and insert "24".

Column 8, Line 39, Claim 20, Delete "17" and insert "24".

Column 8, Line 41, Claim 21, Delete "17" and insert "24".

Column 8, Line 43, Claim 22, Delete "17" and insert "24".

Column 8, Line 45, Claim 23, Delete "17" and insert "24".

Signed and Sealed this

Second Day of February, 1999

Attest:

Attesting Officer

*Acting Commissioner of Patents and Trademarks*